United States Patent
Sakamoto et al.

(10) Patent No.: US 12,240,469 B2
(45) Date of Patent: Mar. 4, 2025

(54) OCCUPANT STATE DETECTION DEVICE AND OCCUPANT STATE DETECTION METHOD

(71) Applicant: Mitsubishi Electric Corporation, Tokyo (JP)

(72) Inventors: Hirotaka Sakamoto, Tokyo (JP); Toshiyuki Hatta, Tokyo (JP); Shintaro Watanabe, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 227 days.

(21) Appl. No.: 17/928,015

(22) PCT Filed: Jul. 9, 2020

(86) PCT No.: PCT/JP2020/026913
§ 371 (c)(1),
(2) Date: Nov. 28, 2022

(87) PCT Pub. No.: WO2022/009401
PCT Pub. Date: Jan. 13, 2022

(65) Prior Publication Data
US 2023/0211791 A1 Jul. 6, 2023

(51) Int. Cl.
*B60W 40/09* (2012.01)
*G06V 20/59* (2022.01)
*G06V 40/20* (2022.01)

(52) U.S. Cl.
CPC ........... *B60W 40/09* (2013.01); *G06V 20/597* (2022.01); *G06V 40/28* (2022.01);
(Continued)

(58) Field of Classification Search
CPC ........... B60W 40/09; B60W 2540/223; B60W 2540/221; B60W 2540/26; G06V 40/28; G06V 20/597
See application file for complete search history.

(56) References Cited

U.S. PATENT DOCUMENTS 10,562,412 B1* 2/2020 Main ................ A61B 5/0205
2011/0210867 A1* 9/2011 Benedikt ................ G08G 1/01
340/905

(Continued)

FOREIGN PATENT DOCUMENTS

JP 2011-123653 A 6/2011
JP 2012-164040 A 8/2012
(Continued)

OTHER PUBLICATIONS

Choi et al., "Driver Drowsiness Detection based on Multimodal using Fusion of Visual-feature and Bio-signal", 2018 International Conference on Information and Communication Technology Convergence (ICTC), 2018, p. 1249-1251.
(Continued)

*Primary Examiner* — Hussein Elchanti
(74) *Attorney, Agent, or Firm* — Birch, Stewart, Kolasch & Birch, LLP

(57) ABSTRACT

Included are: a captured image acquiring unit to acquire a captured image obtained by imaging an occupant; a temperature image acquiring unit to acquire a temperature image indicating a temperature of a surface of a body of the occupant measured in a non-contact manner; a motion detection unit to detect a motion of the occupant on the basis of the captured image; a temperature detection unit to detect a temperature of a hand of the occupant on the basis of the temperature image; and an awakening level estimating unit to estimate an awakening level of the occupant on the basis of the motion of the occupant detected by the motion detection unit and the temperature of the hand of the occupant detected by the temperature detection unit.

5 Claims, 7 Drawing Sheets

(52) U.S. Cl.
CPC . *B60W 2540/221* (2020.02); *B60W 2540/223* (2020.02); *B60W 2540/26* (2013.01)

(56) References Cited

U.S. PATENT DOCUMENTS

| | | | | |
|---|---|---|---|---|
| 2015/0274158 | A1* | 10/2015 | Fujita | B62D 15/025 |
| | | | | 701/23 |
| 2016/0351053 | A1* | 12/2016 | Jung | G08G 1/096791 |
| 2017/0020432 | A1 | 1/2017 | Kusukame et al. | |
| 2017/0197568 | A1* | 7/2017 | DeCia | B60R 16/037 |
| 2018/0220948 | A1 | 8/2018 | Kojima | |
| 2019/0049267 | A1 | 2/2019 | Huang | |
| 2019/0167175 | A1 | 6/2019 | Kojima | |
| 2019/0290180 | A1 | 9/2019 | Kusukame et al. | |
| 2020/0054264 | A1 | 2/2020 | Kojima | |
| 2020/0207358 | A1* | 7/2020 | Katz | G02B 27/0093 |
| 2020/0216095 | A1* | 7/2020 | Isozaki | A61M 21/00 |
| 2020/0330047 | A1 | 10/2020 | Kusukame et al. | |
| 2021/0197832 | A1* | 7/2021 | Matsunami | A61B 5/681 |
| 2021/0275072 | A1 | 9/2021 | Kusukame et al. | |
| 2023/0211791 | A1* | 7/2023 | Sakamoto | G08G 1/16 |
| | | | | 701/1 |

FOREIGN PATENT DOCUMENTS

| | | |
|---|---|---|
| JP | 2017-127616 A | 7/2017 |
| JP | 2018-127112 A | 8/2018 |
| WO | WO 2018/118958 A1 | 6/2018 |

OTHER PUBLICATIONS

International Search Report, issued in PCT/JP2020/026913, PCT/ISA/210, dated Sep. 24, 2020.
Matsuo et al., "Prediction of Drowsy Driving by Monitoring Driver's Behaivor", Proceedings of the 21st International Conference on Pattern Recognition (ICPR2012), Nov. 11-15, 2012, p. 3390-3393.
Pratama et al., "A Review on Driver Drowsiness Based on Image, Bio-Signal, and Driver Behavior", 2017 3rd International Conference on Science and Technology—Computer (ICST), 2017, total 6 pages.
Written Opinion of the International Searching Authority, issued in PCT/JP2020/026913, PCT/ISA/237, dated Sep. 24, 2020.

* cited by examiner

OCCUPANT STATE DETECTION DEVICE AND OCCUPANT STATE DETECTION METHOD

TECHNICAL FIELD

The present disclosure relates to an occupant state detection device and an occupant state detection method.

BACKGROUND ART

Generally, before a person falls asleep, in the body of the person, a blood flow rate in peripheral portions increases in order to lower a deep body temperature. Then, heat is dissipated from the peripheral portions of a human body to the outside of the human body. As a result, the temperature of the peripheral portions of the human body temporarily increases.

Thus, conventionally, a technique for estimating the awakening level of a person on the basis of the temperature of the hand corresponding to the peripheral portion of the human body is known.

For example, Patent Literature 1 discloses a driver awakening level inspection device that determines an awakening level of a driver of a vehicle or the like on the basis of a facial skin temperature, a finger skin temperature, and a pulse rate. The driver awakening level inspection device acquires a finger skin temperature of the driver from a finger temperature sensor disposed at a position on a peripheral edge portion of the steering wheel where the fingers of the driver comes into contact with while the driver holds the steering wheel.

CITATION LIST

Patent Literature

Patent Literature 1: JP 2011-123653 A

SUMMARY OF INVENTION

Technical Problem

In the case of acquiring the temperature of the hand of a person by the method disclosed in Patent Literature 1, there is a problem that the temperature of the hand cannot be acquired if the position where the person grips the handle is shifted.

The present disclosure has been made to solve the above problems, and an object of the present disclosure is to provide an occupant state detection device capable of estimating an awakening level of a person on the basis of a temperature of a hand of the person regardless of a position where the person holds a steering wheel.

Solution to Problem

An occupant state detection device according to the present disclosure includes: processing circuitry configured to acquire a captured image obtained by imaging an occupant; acquire a temperature image indicating a temperature of a surface of a body of the occupant measured in a non-contact manner; detect a motion of the occupant on a basis of the acquired captured image; detect a temperature of a hand of the occupant on a basis of the acquired temperature image; and estimate an awakening level of the occupant on a basis of the detected motion of the occupant and the detected temperature of the hand of the occupant, the motion of the occupant including a motion of the hand of the occupant; estimate the awakening level of the occupant on a basis of the motion of the hand of the occupant when the motion of the hand of the occupant has been detected; and estimate the awakening level of the occupant on a basis of the detected motion of the occupant and the detected temperature of the hand of the occupant when the motion of the hand of the occupant has not been detected.

Advantageous Effects of Invention

According to the present disclosure, it is possible to estimate the awakening level of a person on the basis of a temperature of the hand of the person regardless of the position where the person holds the steering wheel.

DESCRIPTION OF EMBODIMENTS

Hereinafter, an embodiment of the present disclosure will be described in detail with reference to the drawings.

First Embodiment

Figure 1:
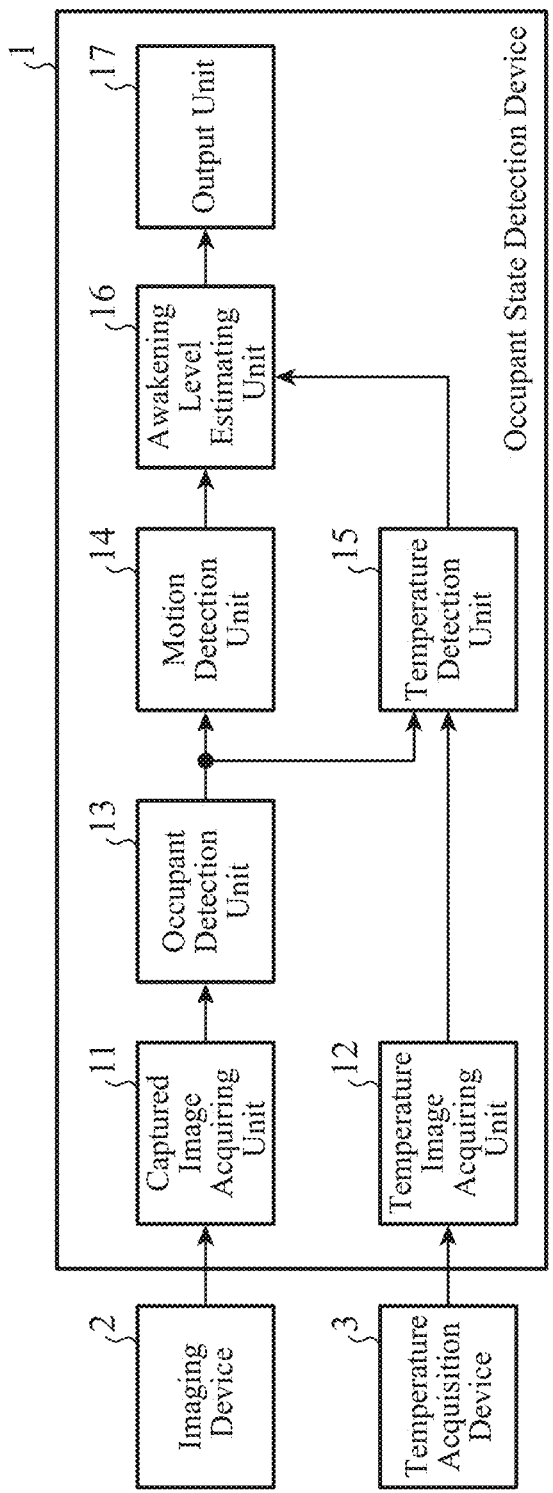
FIG. 1 is a diagram illustrating a configuration example of an occupant state detection device according to a first embodiment.

FIG. 1 is a diagram illustrating a configuration example of an occupant state detection device 1 according to a first embodiment.

The occupant state detection device 1 according to the first embodiment is mounted on a vehicle and estimates an awakening level of an occupant. In the first embodiment, the occupant is assumed to be a driver of the vehicle.

The occupant state detection device 1 is connected to an imaging device 2 and a temperature acquisition device 3.

The imaging device 2 is a camera or the like installed for the purpose of monitoring the inside of the vehicle. The imaging device 2 is installed at least at a position capable of imaging the upper body of the occupant. The imaging device 2 may be shared with, for example, a so-called "Driver Monitoring System; DMS".

The imaging device 2 outputs a captured image (hereinafter referred to as "captured image") to the occupant state detection device 1.

The temperature acquisition device 3 is an infrared camera having a temperature measurement function, an infrared array sensor, or the like. The temperature acquisition device 3 is installed at a position capable of measuring the temperature of the upper body of the occupant including at least the hand of the occupant in a non-contact manner.

The temperature acquisition device 3 outputs an image (hereinafter, referred to as a "temperature image") indicating the measured temperature to the occupant state detection device 1. The temperature image includes temperature information for each pixel. Note that a larger pixel value indicates a higher temperature. Typically, the temperature image output from the temperature acquisition device 3 has a low frame rate.

The occupant state detection device 1 detects the motion of the occupant on the basis of the captured image acquired from the imaging device 2. In addition, the occupant state detection device 1 detects the temperature of the occupant on the basis of the temperature image acquired from the temperature acquisition device 3. The occupant state detection device 1 estimates the awakening level of the occupant on the basis of the detected motion of the occupant and the detected temperature of the occupant. The motion of the occupant and the temperature of the occupant detected by the occupant state detection device 1 will be described later in detail. Details of a method of estimating the awakening level of the occupant by the occupant state detection device 1 will be described later.

The occupant state detection device 1 includes a captured image acquiring unit 11, a temperature image acquiring unit 12, an occupant detection unit 13, a motion detection unit 14, a temperature detection unit 15, an awakening level estimating unit 16, and an output unit 17.

The captured image acquiring unit 11 acquires a captured image output from the imaging device 2.

The captured image acquiring unit 11 outputs the acquired captured image to the occupant detection unit 13.

The temperature image acquiring unit 12 acquires the temperature image output from the temperature acquisition device 3.

The temperature image acquiring unit 12 outputs the acquired temperature image to the temperature detection unit 15.

The occupant detection unit 13 detects information regarding an occupant (hereinafter, referred to as "occupant information") on the basis of the captured image acquired by the captured image acquiring unit 11. Specifically, the occupant detection unit 13 detects the positions of the eyes of the occupant, the position of the mouth of the occupant, the position of the body of the occupant, the position of the hand of the occupant, or the position of the face of the occupant. The occupant detection unit 13 is only required to detect the positions of the eyes of the occupant, the position of the mouth of the occupant, the position of the body of the occupant, the position of the hand of the occupant, or the position of the face of the occupant using a known image recognition technology.

In the first embodiment, the positions of the eyes of the occupant, the position of the mouth of the occupant, the position of the body of the occupant, the position of the hand of the occupant, or the position of the face of the occupant detected by the occupant detection unit 13 is one or more points in an area indicating the eyes of the occupant, the mouth of the occupant, the body of the occupant, the hand of the occupant, or the face of the occupant in the captured image. The position of the eye of the occupant, the position of the mouth of the occupant, the position of the body of the occupant, the position of the hand of the occupant, or the position of the face of the occupant is represented by coordinates on the captured image.

For example, the occupant detection unit 13 detects, as the positions of the eyes of the occupant, the positions of both right and left ends of the occupant's right and left eyes, one point on the upper eyelid, and one point on the lower eyelid.

Furthermore, for example, the occupant detection unit 13 detects, as the position of the mouth of the occupant, the positions of the left and right mouth corners of the occupant, one point on the upper lip, and one point on the lower lip.

Furthermore, for example, the occupant detection unit 13 detects, as the position of the body of the occupant, the positions of the tips of the right and left shoulders of the occupant.

In addition, for example, the occupant detection unit 13 detects, as the position of the hand of the occupant, the positions of one point on the base of the thumb and one point on the base of the little finger.

Further, for example, the occupant detection unit 13 detects, as the position of the face of the occupant, the position of the tip of the jaw of the occupant.

Figure 2:
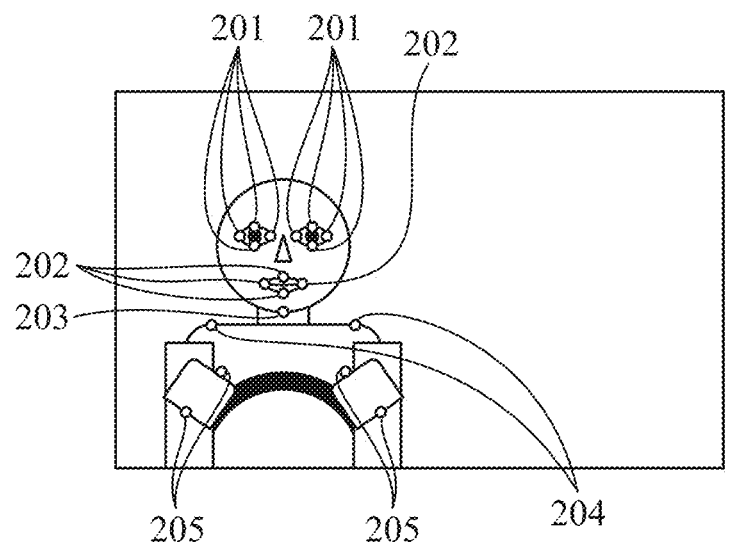
FIG. 2 is a diagram for describing a concept illustrating an example of positions of the eyes of an occupant, a position of the mouth of the occupant, a position of the body of the occupant, positions of the hands of the occupant, or a position of the face of the occupant detected by an occupant detection unit on a captured image in the first embodiment.

Here, FIG. 2 is a diagram for describing a concept illustrating an example of the positions of the eyes of the occupant, the position of the mouth of the occupant, the position of the body of the occupant, the positions of the hands of the occupant, or the position of the face of the occupant detected by the occupant detection unit 13 on the captured image in the first embodiment.

In FIG. 2, eight points indicated by 201 indicate positions of the eyes of the occupant detected by the occupant detection unit 13, here, both right and left ends of the eyes, one point on the upper eyelid, or one point on the lower eyelid. Furthermore, in FIG. 2, four points indicated by 202 indicate positions of the mouth of the occupant detected by the occupant detection unit 13, here, positions of both ends of the mouth corners, one point on the upper lip, or one point on the lower lip. In addition, in FIG. 2, one point indicated by 203 indicates the face of the occupant detected by the occupant detection unit 13, here, the position of the tip of the jaw. Furthermore, in FIG. 2, two points indicated by 204 indicate the positions of the body detected by the occupant detection unit 13, here, the positions of both ends of the shoulder. Furthermore, in FIG. 2, four points indicated by 205 indicate positions of the hands detected by the occupant detection unit 13, here, one point on the base of the thumb or one point on the base of the little finger.

Note that the above-described example is merely an example, and it is possible to appropriately set which point in the area indicating the eye of the occupant, the mouth of the occupant, the body of the occupant, the hand of the occupant, or the face of the occupant in the captured image is set as the position of the eye of the occupant, the position of the mouth of the occupant, the position of the body of the occupant, the position of the hand of the occupant, or the position of the face of the occupant.

The occupant detection unit 13 outputs information indicating the position of the eye of the occupant, the position of the mouth of the occupant, the position of the body of the occupant, the position of the hand of the occupant, or the position of the face of the occupant to the motion detection unit 14 and the temperature detection unit 15. Specifically, the occupant detection unit 13 outputs, to the motion detection unit 14 and the temperature detection unit 15, captured images (hereinafter, referred to as the "captured image after position assignment") to which information that can be identified as the position of the eye of the occupant, the position of the mouth of the occupant, the position of the body of the occupant, the position of the hand of the occupant, or the position of the face of the occupant is added with respect to coordinates indicating the position of the eye of the occupant, the position of the mouth of the occupant, the position of the body of the occupant, the position of the hand of the occupant, or the position of the face of the occupant, respectively.

The motion detection unit 14 detects the motion of the occupant on the basis of the captured image acquired by the captured image acquiring unit 11. Specifically, the motion detection unit 14 detects the motion of the occupant on the basis of the captured image after position assignment output from the occupant detection unit 13. In the first embodiment, as the motion of the occupant, the motion detection unit 14 detects the motion of the eye of the occupant, the motion of the mouth of the occupant, the motion of the body of the occupant, the motion of the hand of the occupant, or the motion of the face of the occupant.

It is assumed that the motion detection unit 14, when acquiring the captured image after position assignment, accumulates the acquired captured image after position assignment in a storage unit (not illustrated) in association with information regarding the acquisition date and time of the captured image after position assignment. Note that the storage unit may be provided in the occupant state detection device 1 or may be provided outside the occupant state detection device 1 in a place that can be referred to by the occupant state detection device 1. The motion detection unit 14 detects the motion of the eye of the occupant, the motion of the mouth of the occupant, the motion of the body of the occupant, the motion of the hand of the occupant, or the motion of the face of the occupant on the basis of the captured image after position assignment output from the occupant detection unit 13 and the past captured image after position assignment accumulated in the storage unit.

Note that, here, as described above, the motion detection unit 14 stores the captured image after position assignment in the storage unit, but this is merely an example. For example, the occupant detection unit 13 may output the captured image after position assignment to the motion detection unit 14 and accumulate the captured image after position assignment in the storage unit, and the motion detection unit 14 may refer to the storage unit and acquire the captured image after position assignment accumulated by the occupant detection unit 13.

For example, the motion detection unit 14 detects that the eyes of the occupant are closed as the motion of the eyes of the occupant on the basis of the position of the eye of the occupant in the captured image after position assignment. Specifically, for example, in a case where the distance between one point on the upper eyelid and one point on the lower eyelid becomes within a preset threshold, the motion detection unit 14 detects that the occupant closes the eyes.

Furthermore, for example, the motion detection unit 14 detects the blink of the occupant as the motion of the eye of the occupant. Specifically, for example, the motion detection unit 14 detects the blink of the occupant on the basis of a change in the distance between one point on the upper eyelid and one point on the lower eyelid.

Note that the above-described example is merely an example, and the motion detection unit 14 is only required to detect that the occupant is closing the eye or that the occupant has blinked using a known technique of detecting opening and closing or blinking of the eye of a person on the basis of an image.

Furthermore, for example, the motion detection unit 14 detects yawning of the occupant as the motion of mouth of the occupant on the basis of the position of mouth of the occupant in the captured image after position assignment. Specifically, for example, in a case where a distance between one point on the upper lip of the occupant and one point on the lower lip of the occupant is separated by a preset threshold (hereinafter, referred to as an "opening determination threshold") or more, the motion detection unit 14 detects that the occupant has yawned. For example, the motion detection unit 14 may detect that the occupant has yawned in a case where a state in which the distance between one point on the upper lip of the occupant and one point on the lower lip of the occupant is equal to or longer than the opening determination threshold has continued for a preset time (hereinafter, referred to as the "opening determination time").

Note that the above-described example is merely an example, and the motion detection unit 14 is only required to detect that the occupant has yawned using a known technique of detecting yawning of a person on the basis of an image.

Furthermore, for example, the motion detection unit 14 detects that the body of the occupant has wobbled as the motion of the body of the occupant on the basis of the position of the body of the occupant in the captured image after position assignment. Specifically, for example, in a case where the position of the body of the occupant in the captured image after position assignment has changed to a position separated by a preset threshold (hereinafter, referred to as "body motion determination threshold") or more, the motion detection unit 14 detects that the body of the occupant has wobbled. For example, in a case where the position of the body of the occupant in the captured image after position assignment has changed by a preset threshold (hereinafter, referred to as a "delta threshold for body motion determination") or more per unit time, the motion detection unit 14 may detect that the body of the occupant has wobbled.

At this time, the motion detection unit 14 also detects the degree of wobble of the body of the occupant. The degree of wobble of the body of the occupant is represented by, for example, an angle (hereinafter, referred to as a "body wobble angle") at which a line connecting the origin on the captured image after position assignment or a predetermined reference point on the captured image after position assignment and the position of the body of the occupant has changed.

Note that, assuming that one point of both ends of the shoulder of the occupant is a first shoulder position and the other point is a second shoulder position, for example, the motion detection unit 14 may detect that the body of occupant has wobbled when either the first shoulder position or the second shoulder position has changed to a position separated by the body motion determination threshold or more, or may detect that the occupant has wobbled when both the first shoulder position and the second shoulder position have changed to a position separated by the body motion determination threshold or more.

Furthermore, for example, the motion detection unit 14 may detect that the body of the occupant has wobbled when either the first shoulder position or the second shoulder position has changed by the delta threshold for body motion determination or more per unit time, or may detect that the body of the occupant has wobbled when both the first shoulder position and the second shoulder position have changed by the delta threshold for body motion determination or more per unit time.

Furthermore, the above-described example is merely an example, and the motion detection unit 14 is only required to detect that the body of the occupant has wobbled and the body wobble angle using a known technique of detecting the body wobble of the person on the basis of the image.

Furthermore, for example, the motion detection unit 14 detects the motion of the hand of the occupant on the basis of the position of the hand of the occupant in the captured image after position assignment. Specifically, for example, in a case where the position of one point on the base of the thumb of the occupant or the position of one point on the base of the little finger of the occupant has changed to a position separated by a preset threshold (hereinafter, referred to as a "hand motion determination threshold") or more, the motion detection unit 14 detects that the hand of the occupant has moved. For example, in a case where a change amount per unit time of the position of one point on the base of the thumb of the occupant or the position of one point on the base of the little finger of the occupant has exceeded a preset threshold (hereinafter, referred to as a "delta threshold for hand motion determination"), the motion detection unit 14 may detect that the hand of the occupant has moved.

Note that the motion detection unit 14 may detect that the hand of the occupant has moved in a case where either the position of one point (hereinafter, referred to as a "thumb point") on the base of the thumb of the occupant or the position of one point (hereinafter, referred to as a "little finger point") on the base of the little finger of the occupant has moved to a position separated by the threshold for hand motion determination or more, or may detect that the hand of the occupant has moved in a case where both the position of the thumb point of the occupant and the position of the little finger point of the occupant have moved to positions separated by the threshold for hand motion determination or more. The motion detection unit 14 may detect that the hand of the occupant has moved when the change amount per unit time of either the position of the thumb point of the occupant or the position of the little finger point of the occupant has exceeded the delta threshold for hand motion determination, or may detect that the hand of the occupant has moved when the change amounts per unit time of both the position of the thumb point of the occupant and the position of the little finger point of the occupant have exceeded the delta threshold for hand motion determination.

For example, in a case where the change in position as described above is one of the right hand and the left hand, the motion detection unit 14 is only required to detect that the hand of the occupant has moved.

Note that the above-described example is merely an example, and the motion detection unit 14 is only required to detect the motion of the hand of the occupant using a known technique of detecting the motion of the hand of the person on the basis of the image.

Furthermore, for example, the motion detection unit 14 detects that the head of the occupant has wobbled as the motion of the face of the occupant on the basis of the position of the face of the occupant in the captured image after position assignment. Specifically, for example, in a case where the position of the face of the occupant in the captured image after position assignment has changed to a position separated by a preset threshold (hereinafter, referred to as a "threshold for face motion determination") or more, the motion detection unit 14 detects that the head of the occupant has wobbled. For example, in a case where the position of the face of the occupant in the captured image after position assignment has changed by a preset threshold (hereinafter, referred to as a "delta threshold for face motion determination") or more per unit time, the motion detection unit 14 may detect that the face of the occupant has wobbled.

At this time, the motion detection unit 14 also detects the degree of wobble of the head of the occupant. The degree of wobble of the head of the occupant is represented by, for example, an angle (hereinafter, referred to as a "head wobble angle") at which a line connecting the origin of the captured image after position assignment or a reference point determined in advance on the captured image after position assignment and the position of the face of the occupant has changed.

Note that the above-described example is merely an example, and the motion detection unit 14 is only required to detect the head wobble of the occupant and the head wobble angle using a known technique of detecting the motion of the face of the person on the basis of the image.

The motion detection unit 14 outputs information (hereinafter, referred to as "motion detection notification information") indicating whether or not the motion of the occupant has been detected on the basis of the captured image acquired by the captured image acquiring unit 11 to the awakening level estimating unit 16. At this time, the motion detection unit 14 outputs the motion detection notification information in association with the information regarding the acquisition date and time of the captured image. Note that the motion detection unit 14 is only required to set the acquisition date and time of the captured image as, for example, the imaging date and time of the captured image assigned to the captured image.

The motion detection notification information includes information on whether or not the motion of the eye of the occupant has been detected, whether or not the motion of the mouth of the occupant has been detected, whether or not the motion of the body of the occupant has been detected, whether or not the motion of the hand of the occupant has been detected, and whether or not the motion of the face of the occupant has been detected.

Specifically, the information on whether or not the motion of the eye of the occupant is detected is, for example, information on whether or not it is detected that the occupant has closed the eyes and whether or not it is detected that the occupant has blinked.

The information on whether or not the motion of the mouth of the occupant has been detected is specifically, for example, information on whether or not it is detected that the occupant has yawned.

Specifically, the information on whether or not the motion of the body of the occupant has been detected is, for example, information on whether or not the body of the occupant has been detected to be wobbled, and information on a body wobble angle when the body of the occupant has been detected to be wobbled.

The information on whether or not the motion of the hand of the occupant has been detected may include, for example, in addition to the information on whether or not the motion of the hand of the occupant has been detected, information capable of identifying whether the motion of the hand of the occupant is the right hand or the left hand when the motion of the hand of the occupant is detected.

The information on whether or not the motion of the face of the occupant has been detected is, for example, information on whether or not the head of the occupant has been detected to be wobbled, and information on the head wobble angle when the head of the occupant has been detected to be wobbled.

The temperature detection unit 15 detects the temperature of the occupant on the basis of the captured image after position assignment output from the occupant detection unit 13 and the temperature image acquired by the temperature image acquiring unit 12. In the first embodiment, the temperature of the occupant refers to the temperature of the hand and the temperature of the face of the occupant. That is, the temperature detection unit 15 detects the temperature of the hand and the temperature of the face of the occupant on the basis of the captured image after position assignment output from the occupant detection unit 13 and the temperature image acquired by the temperature image acquiring unit 12.

Specifically, first, the temperature detection unit 15 aligns the captured image after position assignment and the temperature image. In the first embodiment, the alignment of the captured image after position assignment and the temperature image performed by the temperature detection unit 15 means that pixels indicating the same spatial position are associated with each other for the captured image after position assignment and the temperature image.

Since each of the imaging device 2 and the temperature acquisition device 3 is fixedly installed in the vehicle, the temperature detection unit 15 can align the captured image after position assignment and the temperature image on the basis of the predetermined installation position of the imaging device 2 and the predetermined installation position of the temperature acquisition device 3. Then, when aligning the captured image after position assignment and the temperature image, the temperature detection unit 15 can specify which pixel in the temperature image indicates the temperature of the hand of the occupant or the temperature of the face of the occupant.

Figure 3:
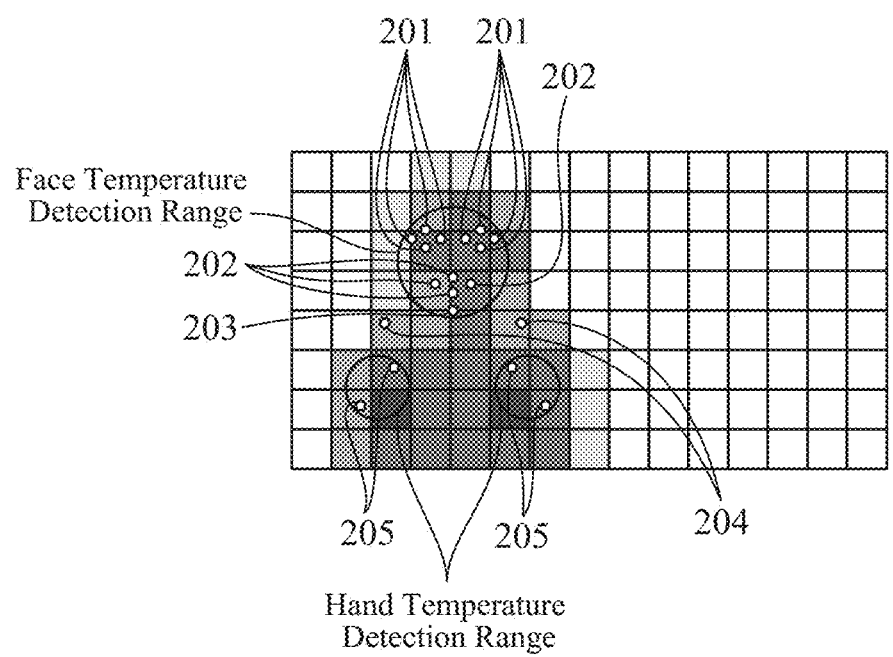
FIG. 3 is a diagram illustrating an example of a concept of a temperature image after a temperature detection unit performs alignment with a captured image after position assignment in the first embodiment.

Here, FIG. 3 is a diagram illustrating an example of a concept of a temperature image after the temperature detection unit 15 performs alignment with a captured image after position assignment in the first embodiment.

For convenience, FIG. 3 illustrates the temperature image by reflecting the positions of the eyes of the occupant (see 201 in FIG. 3), the position of the mouth of the occupant (see 202 in FIG. 3), the position of the face of the occupant (see 203 in FIG. 3), the position of the body of the occupant (see 204 in FIG. 3), and the positions of the hands of the occupant (see 205 in FIG. 3) specified from the captured image after position assignment on the temperature image. Note that, here, it is assumed that the captured image after position assignment is the captured image after position assignment output from the occupant detection unit 13 in a case where the occupant detection unit 13 detects the position of the face of the occupant, the position of the mouth of the occupant, the positions of the eyes of the occupant, the positions of the hands of the occupant, and the position of the body of the occupant as illustrated in FIG. 2.

For example, the temperature detection unit 15 sets a range indicated by a minimum circle passing through the position of the face of the occupant, in other words, the position of the chin of the occupant and including the positions of the eyes of the occupant and the position of the mouth of the occupant on the temperature image as a range (hereinafter, referred to as a "face temperature detection range") for detecting the temperature of the face of the occupant. Note that in the first embodiment, "minimum" is not limited to strictly "minimum", and may be substantially minimum. In addition, the method for setting the face temperature detection range is merely an example. It is possible to appropriately set what range the temperature detection unit 15 sets as the face temperature detection range.

The temperature detection unit 15 detects, for example, an average value of pixel values of pixels at least a part of which is included in the face temperature detection range as the temperature of the face of the occupant.

Note that the method of detecting the temperature of the face of the occupant as described above is merely an example, and the temperature detection unit 15 may detect the temperature of the face of the occupant by another method. For example, the temperature detection unit 15 may select pixels (hereinafter, referred to as a "face selection pixel") having the largest area within the face temperature detection range from among a plurality of pixels at least a part of which is included in the face temperature detection range, and detect the pixel value of the face selection pixel as the temperature of the face of the occupant. In a case where there is a plurality of face selection pixels, the temperature detection unit 15 detects, for example, a pixel value of any face selection pixel among the plurality of face selection pixels as the temperature of the face of the occupant.

Furthermore, the temperature detection unit 15 sets, for example, a range indicated by a circle passing through the position of the hand of the occupant, in other words, one point on the base of the thumb and one point of the base of the little finger of the occupant on the temperature image and having these two points as a diameter, as a range (hereinafter, referred to as a "hand temperature detection range") for detecting the temperature of the hand of the occupant. The temperature detection unit 15 sets a hand temperature detection range for each of the right hand and the left hand. Note that the above-described method for setting the hand temperature detection range is merely an example. It is possible to appropriately set what range the temperature detection unit 15 sets as the hand temperature detection range.

The temperature detection unit 15 detects, for example, an average value of pixel values of pixels at least a part of which is included in the hand temperature detection range as the temperature of the hand of the occupant.

Note that the method of detecting the temperature of the hand of the occupant as described above is merely an example, and the temperature detection unit 15 may detect the temperature of the hand of the occupant by another method. For example, the temperature detection unit 15 may select pixels (hereinafter, referred to as a "hand selection pixel") having the largest area within the hand temperature detection range from among a plurality of pixels at least a part of which is included in the hand temperature detection range, and detect the pixel value of the hand selection pixel as the temperature of the hand of the occupant. In a case where there is a plurality of hand selection pixels, the temperature detection unit 15 detects, for example, a pixel value of any hand selection pixel among the plurality of hand selection pixels as the temperature of the hand of the occupant.

The temperature detection unit 15, when detecting the temperature of the hand and the temperature of the face of the occupant, outputs information (hereinafter, referred to as "temperature detection information") regarding the detected temperature of the hand and temperature of the face of the occupant to the awakening level estimating unit 16 in association with the information regarding the acquisition date and time of the temperature image. The temperature detection unit 15 is only required to set the acquisition date and time of the temperature image as, for example, the creation date and time of the temperature image assigned to the temperature image.

The awakening level estimating unit 16 estimates the awakening level of the occupant on the basis of the motion of the occupant detected by the motion detection unit 14 and the temperature of the hand and the temperature of the face of the occupant detected by the temperature detection unit 15. In the first embodiment, as an example, the awakening level estimating unit 16 sets the awakening level to a degree indicated in five levels of "level 1" to "level 5". Note that the greater the awakening level, the higher the degree that the occupant is awakened. A method by which the awakening level estimating unit 16 estimates the awakening level of the occupant will be described in detail below.

The awakening level estimating unit 16 first determines whether or not the motion detection unit 14 has detected the motion of the hand of the occupant. Specifically, the awakening level estimating unit 16 determines whether or not motion detection notification information including information indicating that a motion of a hand has been detected has been output from the motion detection unit 14.

When the motion detection unit 14 has detected the motion of the hand of the occupant, the awakening level estimating unit 16 estimates the awakening level of the occupant on the basis of the motion of the hand of the occupant. Specifically, the awakening level estimating unit 16 estimates that the occupant is in an awakening state because the hand of the occupant has moved, and sets the awakening level of the occupant to "level 5". Note that the presence of the motion of the hand of the occupant means that the occupant is highly likely to be awakening.

On the other hand, in a case where the motion detection unit 14 has not detected the motion of the hand of the occupant, the awakening level estimating unit 16 estimates the awakening level of the occupant on the basis of the motion of the occupant detected by the motion detection unit 14 and the temperature of the hand and the temperature of the face of the occupant detected by the temperature detection unit 15. Specifically, the awakening level estimating unit 16 estimates the awakening level of the occupant in accordance with a rule (hereinafter, referred to as "awakening level estimating rule") constructed on the basis of a preset condition (hereinafter, referred to as "determination condition"). The awakening level estimating rule is constructed in advance by a combination of logical sum or logical product of the determination conditions.

It can be said that there is a high possibility that the awakening level of the occupant is reduced when there is no motion of the hand of the occupant.

The determination condition and the awakening level estimating rule will be described with specific examples.

As the determination condition, for example, the following conditions (A) to (E) are defined.

(A) The number of times "the occupant blinks" in the past 10 seconds is equal to or greater than five.

(B) The time during which "the occupant closes his/her eyes" in the past 10 seconds is equal to or greater than five seconds.

(C) The number of times "the occupant yawns" in the past five minutes is one or more.

(D) The number of times "the head of the occupant wobbles" at an angle equal to or greater than 20 degrees in the past five minutes is equal to or greater than two times.

(E) The temperature of the hand of the occupant with respect to the temperature of the face of the occupant is within −5° C.

(A) to (D) are conditions for determining the motion of the occupant appearing when the occupant feels drowsy. When (A) to (D) are satisfied, it can be said that the occupant feels drowsy. Note that, in a case where (D) has the content as described above, it can be determined from the head wobble angle that "the head of the occupant wobbles" at an angle equal to or greater than 20 degrees.

(E) is a condition for determining that a physiological phenomenon in which the blood flow rate at the peripheral portion such as the fingertip increases and the temperature of the peripheral portion rises to be close to the face or the deep body temperature occurs when the person feels drowsy. When (E) is satisfied, it can be said that the occupant feels drowsy.

In a case where the determination conditions are the above (A) to (E), for example, the following rules (1) to (6) are constructed as the awakening level estimating rule.

(1) If the determination condition (E) is false, the awakening level "level 5"

(2) If the determination condition (E) is true and the other determination conditions (determination conditions (A) to (D)) are false, the awakening level "level 5"

(3) If the determination condition (E) is true and one of the other determination conditions (determination conditions (A) to (D)) is true, the awakening level "level 4"

(4) If the determination condition (E) is true and two of the other determination conditions (determination conditions (A) to (D)) are true, the awakening level "level 3".

(5) If the determination condition (E) is true and three of the other determination conditions (determination conditions (A) to (D)) are true, the awakening level "level 2".

(6) If the determination condition (E) is true and all the other determination conditions (determination conditions (A) to (D)) are true, the awakening level "level 1".

For example, it is assumed that the awakening level estimating unit 16, when acquiring motion detection notification information from the motion detection unit 14, accumulates the motion detection notification information in the storage unit. In addition, it is assumed that the awakening level estimating unit 16, when acquiring temperature detection information from the temperature detection unit 15, accumulates the temperature detection information in the storage unit. The awakening level estimating unit 16 estimates the awakening level of the occupant in accordance with the awakening level estimating rule on the basis of the motion detection notification information and the temperature detection information accumulated in the storage unit.

Note that, here, as described above, the awakening level estimating unit 16 stores the motion detection notification information and the temperature detection information, but this is merely an example. For example, the motion detection unit 14 may accumulate the motion detection notification information in the storage unit, the temperature detection unit 15 may accumulate the temperature detection information in the storage unit, and the awakening level estimating unit 16 may estimate the awakening level of the occupant with reference to the storage unit.

The determination conditions are merely an example. For example, a determination condition related to a body motion such as "the number of times "the body of the occupant wobbles" at an angle equal to or greater than 20 degrees in the past five minutes is equal to or greater than two times" may be added to the determination conditions.

The content of the determination condition is experimentally determined in advance. Then, the awakening level estimating rule is constructed in advance using the determination condition experimentally determined in advance.

As described above, the awakening level estimating unit 16 first determines whether or not the motion of the hand of the occupant has been detected, and estimates that the occupant is in the awakening state, in other words, the awakening level of the occupant is "level 5" when the motion of the hand of the occupant has been detected. In this case, the awakening level estimating unit 16 does not estimate the awakening level of the occupant in accordance with the awakening level estimating rule, in other words, does not estimate the awakening level of the occupant using the temperature of the hand and the temperature of the face. As a specific example, for example, in a case where the occupant is performing the steering wheel operation, since the motion of the hand of the occupant is detected by the motion detection unit 14, the awakening level estimating unit 16 estimates that the occupant is in the awakening state, and does not estimate the awakening level of the occupant using the temperature of the hand and the temperature of the face of the occupant.

When the motion of the hand of the occupant is not detected, the awakening level estimating unit 16 estimates the awakening level of the occupant using the motion of the occupant and the temperature of the hand and the temperature of the face of the occupant.

Typically, the temperature image output from the temperature acquisition device 3 has a low frame rate. Therefore, when there is motion in the hand of the occupant, blurring is likely to occur in the temperature image, and conversely, when there is no motion in the hand of the occupant, blurring is less likely to occur in the temperature image. Therefore, in a case where there is no motion in the hand of the occupant, the temperature detection unit 15 can accurately detect the temperature of the hand and the temperature of the face of the occupant from the temperature image as compared with a case there is motion in the hand of the occupant.

The awakening level estimating unit 16 can reasonably estimate the awakening level of the occupant using the temperature of the hand and the temperature of the face of the occupant detected on the basis of the temperature image by estimating the awakening level of the occupant in the order as described above.

The awakening level estimating unit 16 outputs information (hereinafter referred to as "awakening level information") regarding the estimated awakening level of the occupant to the output unit 17. The awakening level information includes, for example, information on the level of the awakening level determined by the awakening level estimating unit 16.

The output unit 17 outputs the awakening level information output from the awakening level estimating unit 16. Specifically, the output unit 17 outputs the awakening level information to, for example, an alarm output control device (not illustrated), an air conditioning control device (not illustrated), or an automatic driving control device (not illustrated). The alarm output control device, the air conditioning control device, and the automatic driving control device are mounted on a vehicle.

For example, when the awakening level information is output from the awakening level estimating unit 16, the alarm output control device outputs an alarm for calling attention to drowsiness to the occupant in the vehicle.

For example, when the awakening level information is output from the awakening level estimating unit 16, the air conditioning control device controls air conditioning to suppress drowsiness.

For example, when the awakening level information is output from the awakening level estimating unit 16, the automatic driving control device switches the driving control method of the vehicle from the manual driving to the automatic driving. In this case, the vehicle has an automatic driving function. Even when the vehicle has an automatic driving function, the driver can manually drive the vehicle by himself/herself.

An operation of the occupant state detection device 1 according to the first embodiment will be described.

Figure 4:
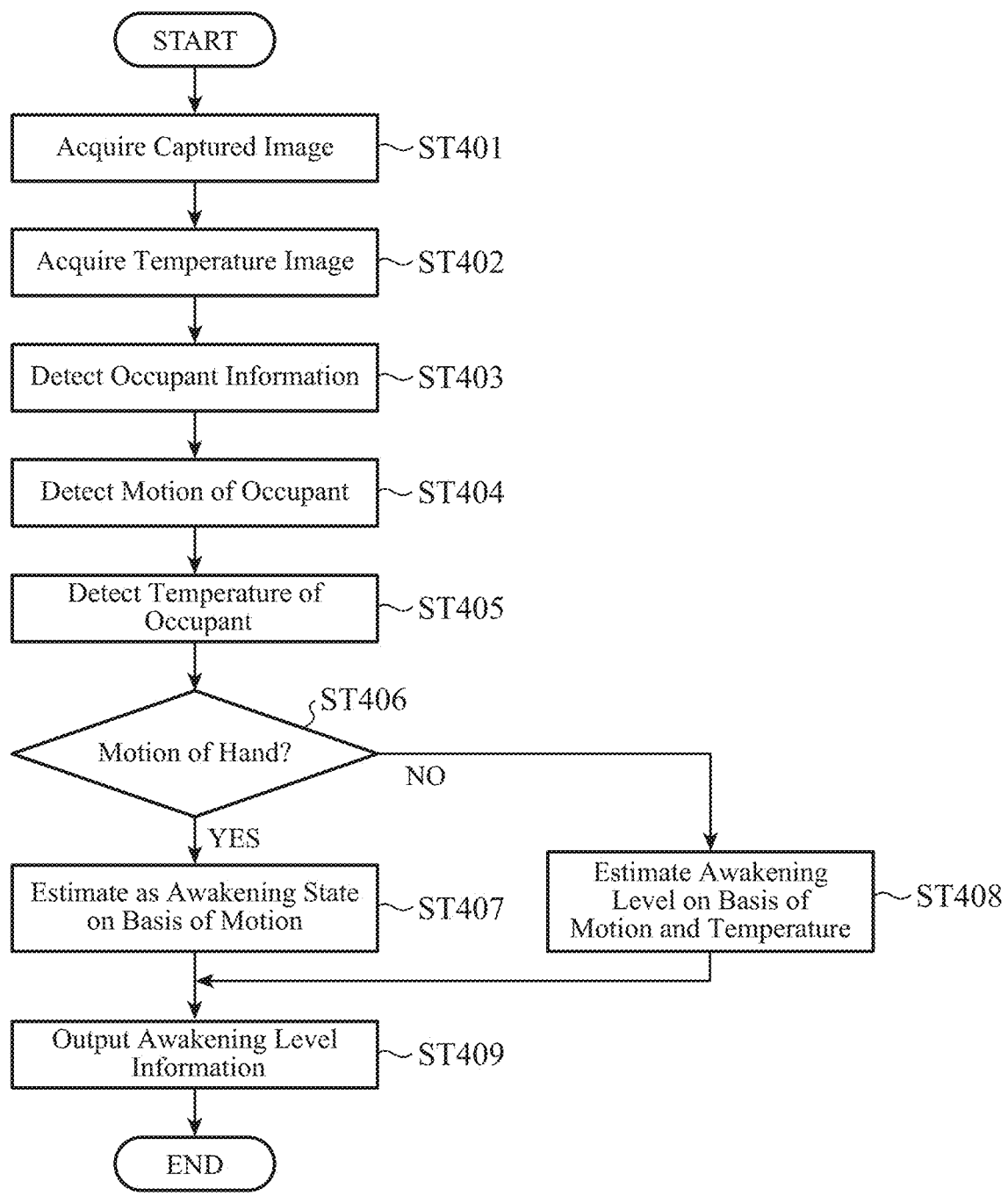
FIG. 4 is a flowchart for explaining an operation of the occupant state detection device according to the first embodiment.

FIG. 4 is a flowchart for explaining the operation of the occupant state detection device 1 according to the first embodiment.

The captured image acquiring unit 11 acquires the captured image output from the imaging device 2 (step ST401).

The captured image acquiring unit 11 outputs the acquired captured image to the occupant detection unit 13.

The temperature image acquiring unit 12 acquires the temperature image output from the temperature acquisition device 3 (step ST402).

The temperature image acquiring unit 12 outputs the acquired temperature image to the temperature detection unit 15.

The occupant detection unit 13 detects occupant information on the basis of the captured image acquired by the captured image acquiring unit 11 in step ST401 (step ST403). Specifically, the occupant detection unit 13 detects the position of the eye of the occupant, the position of the mouth of the occupant, the position of the body of the occupant, the position of the hand of the occupant, or the position of the face of the occupant.

The occupant detection unit 13 outputs information indicating the position of the eye of the occupant, the position of the mouth of the occupant, the position of the body of the occupant, the position of the hand of the occupant, or the position of the face of the occupant to the motion detection unit 14 and the temperature detection unit 15. Specifically, the occupant detection unit 13 outputs the captured image after position assignment to the motion detection unit 14 and the temperature detection unit 15.

The motion detection unit 14 detects the motion of the occupant on the basis of the captured image acquired by the captured image acquiring unit 11 in step ST401 (step ST404). Specifically, the motion detection unit 14 detects the motion of the occupant on the basis of the captured image after position assignment output from the occupant detection unit 13 in step ST403.

The motion detection unit 14 outputs the motion detection notification information to the awakening level estimating unit 16 in association with the information regarding the acquisition date and time of the captured image.

The temperature detection unit 15 detects the temperature of the occupant on the basis of the captured image after position assignment output from the occupant detection unit 13 in step ST403 and the temperature image acquired by the temperature image acquiring unit 12 in step ST402 (step ST405). Specifically, the temperature detection unit 15 detects the temperature of the hand and the temperature of the face of the occupant on the basis of the captured image after position assignment output from the occupant detection unit 13 and the temperature image acquired by the temperature image acquiring unit 12.

The temperature detection unit 15, when detecting the temperature of the hand and the temperature of the face of the occupant, outputs the temperature detection information to the awakening level estimating unit 16 in association with the information regarding the acquisition date and time of the temperature image.

The awakening level estimating unit 16 first determines whether or not the motion detection unit 14 has detected the motion of the hand of the occupant in step ST404 (step ST406). Specifically, the awakening level estimating unit 16 determines whether or not motion detection notification information including information indicating that a motion of a hand has been detected has been output from the motion detection unit 14.

When the motion detection unit 14 detects the motion of the hand of the occupant ("YES" in step ST406), the awakening level estimating unit 16 estimates the awakening level of the occupant on the basis of the motion of the hand of the occupant. Specifically, the awakening level estimating unit 16 estimates that the occupant is in the awakening state because there is the motion of the hand of the occupant, and sets the awakening level of the occupant to "level 5" (step ST407). The awakening level estimating unit 16 outputs the awakening level information to the output unit 17. Then, the operation of the occupant state detection device 1 proceeds to step ST409.

On the other hand, if the motion detection unit 14 has not detected the motion of the hand of the occupant ("NO" in step ST406), the awakening level estimating unit 16 estimates the awakening level of the occupant on the basis of the motion of the occupant detected by the motion detection unit 14 in step ST404 and the temperature of the hand and the temperature of the face of the occupant detected by the temperature detection unit 15 in step ST405 (step ST408). Specifically, the awakening level estimating unit 16 estimates the awakening level of the occupant in accordance with the awakening level estimating rule constructed on the basis of the determination condition.

The awakening level estimating unit 16 outputs the awakening level information to the output unit 17. Then, the operation of the occupant state detection device 1 proceeds to step ST409.

In step ST409, the output unit 17 outputs the awakening level information output from the awakening level estimating unit 16 (step ST409).

Note that, in the flowchart of FIG. 4, the operation of the occupant state detection device 1 is performed in the order of step ST401 and step ST402, but this is merely an example. The order of the operation of step ST401 and the operation of step ST402 may be reversed or may be performed in parallel. Furthermore, it suffices that the operation of step ST402 is performed before the operation of step ST405 is performed.

In addition, in the flowchart of FIG. 4, the operation of the occupant state detection device 1 is performed in the order of step ST404 and step ST405, but this is merely an example. The order of the operation of step ST404 and the operation of step ST405 may be reversed or may be performed in parallel.

In the related art as described above, the temperature of the hand of the occupant used for estimating the awakening level of the occupant of the vehicle is acquired from the finger temperature sensor disposed at the position of the peripheral edge of the steering wheel with which the finger of the driver comes into contact while the driver holds the steering wheel. When the temperature of the hand of the occupant is acquired by the method disclosed in the related art, the temperature of the hand cannot be acquired if the position where the occupant holds the steering wheel is shifted. In addition, since the occupant is required to take a constant posture, the method of acquiring the temperature of the hand of the occupant as disclosed in the related art is a method that imposes a load on the occupant.

On the other hand, the occupant state detection device 1 acquires the captured image obtained by imaging the occupant and the temperature image indicating the temperature of the surface of the body of the occupant measured in a non-contact manner, and estimates the awakening level of the occupant on the basis of the motion of the occupant detected on the basis of the captured image and the temperature of the hand and the temperature of the face of the occupant detected on the basis of the temperature image.

As a result, the occupant state detection device 1 can estimate the awakening level of the occupant on the basis of the temperature of the hand and the temperature of the face of the occupant regardless of the position where the occupant holds the steering wheel.

Further, the occupant state detection device 1 first determines whether or not the motion of the hand of the occupant has been detected when estimating the awakening level of the occupant, estimates the awakening level of the occupant on the basis of the motion of the hand of the occupant when the motion of the hand of the occupant has been detected, and estimates the awakening level of the occupant on the basis of the motion of the occupant, the temperature of the hand of the occupant, and the temperature of the face of the occupant when the motion of the hand of the occupant has not been detected.

As a result, the occupant state detection device 1 can reasonably estimate the awakening level of the occupant using the temperature of the hand and the temperature of the face of the occupant detected on the basis of the temperature image.

In the first embodiment described above, when the motion of the hand is not detected, the awakening level estimating unit 16 estimates the awakening level of the occupant on the basis of the motion of the occupant detected by the motion detection unit 14 and the temperature of the hand and the temperature of the face of the occupant detected by the temperature detection unit 15. Specifically, for example, as in the determination condition (E) of the above-described example, the awakening level estimating unit 16 detects the relative temperature change of the hand on the basis of the temperature of the hand and the temperature of the face of the occupant, and uses the relative temperature change of the hand for estimation of the awakening level of the occupant. However, this is merely an example.

The awakening level estimating unit 16 does not need to use the temperature of the face of the occupant when estimating the awakening level of the occupant. That is, in a case where the motion of the hand is not detected, the awakening level estimating unit 16 may estimate the awakening level of the occupant on the basis of the motion of the occupant detected by the motion detection unit 14 and the temperature of the hand of the occupant detected by the temperature detection unit 15. For example, in the above example, the determination condition (E) may be a condition for a change in the temperature of the hand of the occupant.

The temperature of the occupant used when the awakening level estimating unit 16 estimates the awakening level of the occupant may be at least the temperature of the hand of the occupant. Note that, in this case, the temperature detection unit 15 only needs to detect the temperature of the hand of the occupant as the temperature of the occupant.

However, for example, in a case where the temperature acquisition device 3 is a non-contact temperature array sensor such as a thermopile, the temperature array sensor has a feature that a temperature detection error in units of pixels is large and a temperature detection error in a difference between a certain pixel and other pixels is small. Therefore, the temperature change of the hand of the occupant when the awakening level of the occupant is estimated can be detected more accurately by detecting the temperature change of the hand of the occupant from the difference between the temperature of the hand of the occupant and the temperature of the face of the occupant using the temperature of the face of the occupant instead of detecting the temperature change of the hand of the occupant only from the temperature of the hand of the occupant. As a result, the awakening level estimating unit 16 can estimate the awakening level of the occupant more accurately.

In addition, in the first embodiment described above, when the motion detection unit 14 has not detected the motion of the hand of the occupant, the awakening level estimating unit 16 estimates the awakening level of the occupant in accordance with the awakening level estimating rule constructed on the basis of the determination condition. Not limited to this, in a case where the motion detection unit 14 has not detected the motion of the hand of the occupant, the awakening level estimating unit 16 can also estimate the awakening level of the occupant on the basis of a learned model (hereinafter, referred to as a "machine learning model") in machine learning, and thus, it will be described below.

Figure 5:
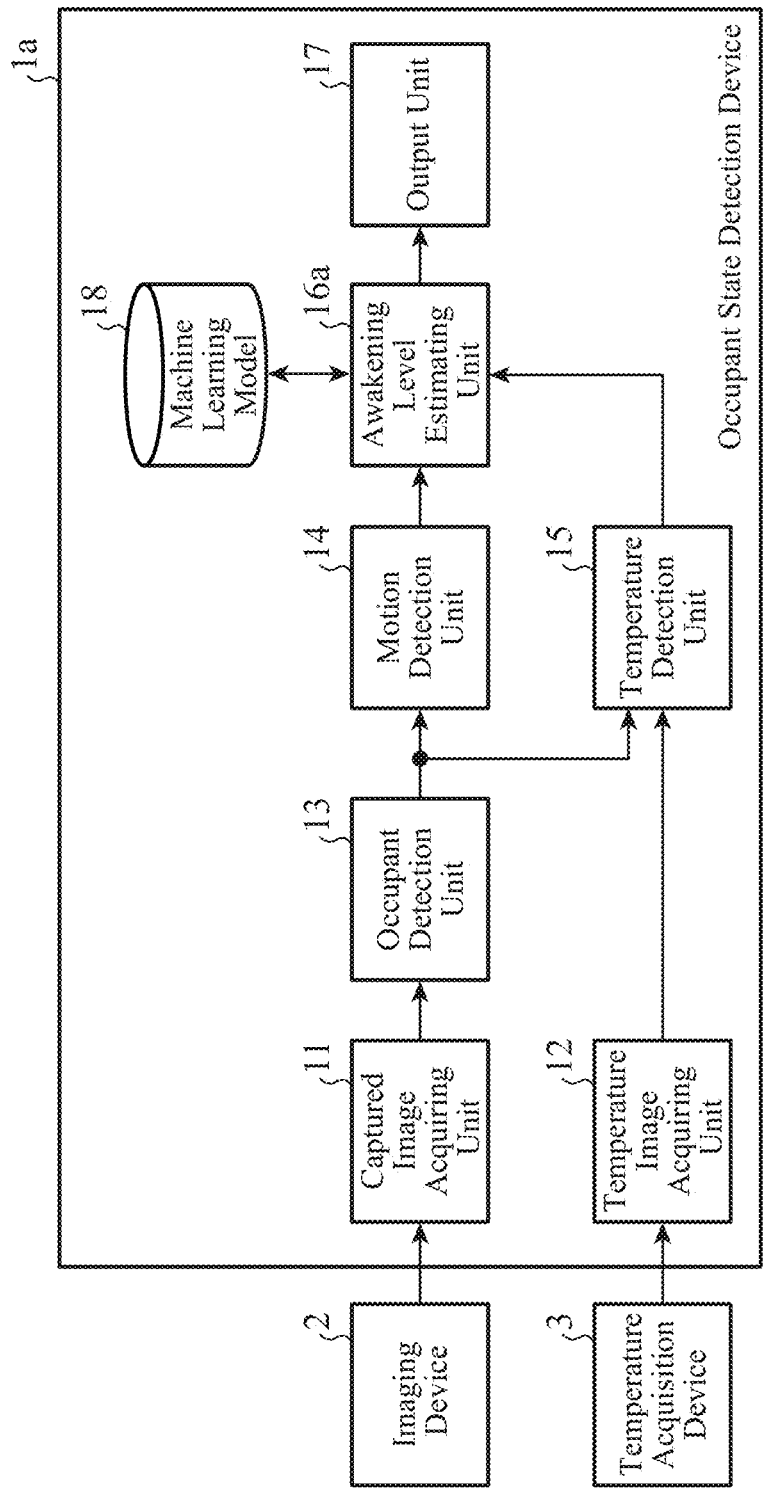
FIG. 5 is a diagram illustrating a configuration example of the occupant state detection device in a case where the occupant state detection device estimates an awakening level of an occupant on the basis of a machine learning model in the first embodiment.

FIG. 5 is a diagram illustrating a configuration example of an occupant state detection device 1a in a case where the occupant state detection device 1a estimates the awakening level of the occupant on the basis of a machine learning model 18 in the first embodiment.

In the occupant state detection device 1a illustrated in FIG. 5, the same components as those of the occupant state detection device 1 described with reference to FIG. 1 are denoted by the same reference numerals, and redundant description is omitted.

The occupant state detection device 1a is different from the occupant state detection device 1 described with reference to FIG. 1 in that the occupant state detection device 1a includes the machine learning model 18.

In the occupant state detection device 1a, the specific operation of an awakening level estimating unit 16a is different from the specific operation of the awakening level estimating unit 16 in the occupant state detection device 1.

The machine learning model 18 is a machine learning model that uses information regarding the motion of the occupant and information regarding the temperature of the hand and the temperature of the face of the occupant as inputs, and outputs information indicating a degree of awakening of the occupant. The information regarding the motion of the occupant includes information regarding the motion of eye of the occupant, the motion of mouth of the occupant, the motion of body of the occupant, the motion of hand of the occupant, or the motion of face of the occupant.

The machine learning model 18 is generated in advance by learning using teacher data and a correct answer label of the awakening level. The correct answer label of the awakening level is, for example, a level indicating the awakening level. The correct answer label may be, for example, a drowsiness evaluation index from a facial expression by the New Energy and Industrial Technology Development Organization (NEDO), or may be a level of the degree of drowsiness indicated by the Karolinska Sleepiness Scale (KSS). In addition, the correct answer label may be, for example, a level indicating the awakening level uniquely set by an administrator of the occupant state detection device 1a.

Note that, here, as illustrated in FIG. 5, the machine learning model 18 is provided in the occupant state detection device 1a, but this is merely an example. The machine learning model 18 may be provided outside the occupant state detection device 1a at a place that can be referred to by the occupant state detection device 1a.

The awakening level estimating unit 16a estimates the awakening level of the occupant on the basis of the motion of the occupant detected by the motion detection unit 14, the temperature of the hand and the temperature of the face of the occupant detected by the temperature detection unit 15, and the machine learning model 18.

The awakening level estimating unit 16a first determines whether or not the motion detection unit 14 has detected the motion of the hand of the occupant. Specifically, the awakening level estimating unit 16a determines whether or not the motion detection notification information including the information indicating that the motion of the hand is detected is output from the motion detection unit 14.

When the motion detection unit 14 has detected the motion of the hand of the occupant, the awakening level estimating unit 16a estimates the awakening level of the occupant on the basis of the motion of the hand of the occupant. Specifically, the awakening level estimating unit 16a estimates that the occupant is in the awakening state because there is the motion of the hand of the occupant, and sets the awakening level of the occupant to "level 5". Note that the presence of the motion of the hand of the occupant means that the occupant is highly likely to be awakening.

On the other hand, when the motion detection unit 14 has not detected the motion of the hand of the occupant, the awakening level estimating unit 16a estimates the awakening level of the occupant on the basis of the motion of the occupant detected by the motion detection unit 14, the temperature of the hand and the temperature of the face of the occupant detected by the temperature detection unit 15, and the machine learning model 18. Specifically, the awakening level estimating unit 16a inputs the motion detection notification information output from the motion detection unit 14 and the temperature detection information output from the temperature detection unit 15 to the machine learning model 18, and acquires information indicating the awakening level of the occupant.

The operation of the occupant state detection device 1a configured as illustrated in FIG. 5 will be described.

The operation of the occupant state detection device 1a configured as illustrated in FIG. 5 is different from the operation of the occupant state detection device 1 described with reference to the flowchart of FIG. 4 in the specific operation in step ST408. Other specific operations (specific operations in steps ST401 to ST407 and step ST409) have already been described, and thus duplicate description will be omitted. Note that, in the occupant state detection device 1a, the specific operation in step ST407 is an operation in which the operation of the awakening level estimating unit 16, which has been already described, is replaced with the operation of the awakening level estimating unit 16a.

In the occupant state detection device 1a, when the motion detection unit 14 has not detected the motion of the hand of the occupant ("NO" in step ST406), the awakening level estimating unit 16a estimates the awakening level of the occupant on the basis of the motion of the occupant detected by the motion detection unit 14 in step ST404, the temperature of the hand and the temperature of the face of the occupant detected by the temperature detection unit 15 in step ST405, and the machine learning model 18 (step ST408). Specifically, the awakening level estimating unit 16a inputs the motion detection notification information output from the motion detection unit 14 and the temperature detection information output from the temperature detection unit 15 to the machine learning model 18, and acquires information indicating the awakening level of the occupant.

The awakening level estimating unit 16a outputs the awakening level information to the output unit 17. Then, the operation of the occupant state detection device 1 proceeds to step ST409.

As described above, the occupant state detection device 1a acquires the captured image obtained by imaging the occupant and the temperature image indicating the temperature of the surface of the body of the occupant measured in a non-contact manner, and estimates the awakening level of the occupant on the basis of the motion of the occupant detected on the basis of the captured image, the temperature of the hand and the temperature of the face of the occupant detected on the basis of the temperature image, and the machine learning model 18.

As a result, the occupant state detection device 1a can estimate the awakening level of the occupant on the basis of the temperature of the hand of the occupant regardless of the position where the occupant holds the steering wheel.

In addition, the occupant state detection device 1a first determines whether or not the motion of the hand of the occupant has been detected when estimating the awakening level of the occupant, estimates the awakening level of the occupant on the basis of the motion of the hand of the occupant in a case where the motion of the hand of the occupant has been detected, and estimates the awakening level of the occupant on the basis of the motion of the occupant, the temperature of the hand of the occupant, the temperature of the face of the occupant, and the machine learning model 18 in a case where the motion of the hand of the occupant has not been detected.

As a result, the occupant state detection device 1a can reasonably estimate the awakening level of the occupant using the temperatures of the hand and the face of the occupant detected on the basis of the temperature image.

In addition, since the occupant state detection device 1a estimates the awakening level of the occupant using the machine learning model 18, if a large number of pieces of teacher data can be prepared, the estimation accuracy of the awakening level of the occupant can be enhanced as compared with the estimation of the awakening level of the occupant in accordance with the awakening level estimating rule.

Note that, also in the occupant state detection device 1a, the awakening level estimating unit 16a does not need to use the temperature of the face of the occupant when estimating the awakening level of the occupant. That is, in a case where the motion of the hand is not detected, the awakening level estimating unit 16a may estimate the awakening level of the occupant on the basis of the motion of the occupant detected by the motion detection unit 14, the temperature of the hand of the occupant detected by the temperature detection unit 15, and the machine learning model 18. As described above, the temperature of the occupant used when the awakening level estimating unit 16a estimates the awakening level of the occupant is only required to be at least the temperature of the hand of the occupant. Note that, in this case, the temperature detection unit 15 only needs to detect the temperature of the hand of the occupant as the temperature of the occupant.

In this case, the machine learning model 18 is a machine learning model that uses information regarding the motion of the occupant and information regarding the temperature of the hand of the occupant as inputs, and outputs information indicating the degree of awakening of the occupant.

In addition, in the first embodiment described above, the occupant state detection device 1 can also be configured to estimate the awakening level of the occupant in consideration of the attribute of the occupant.

Figure 6:
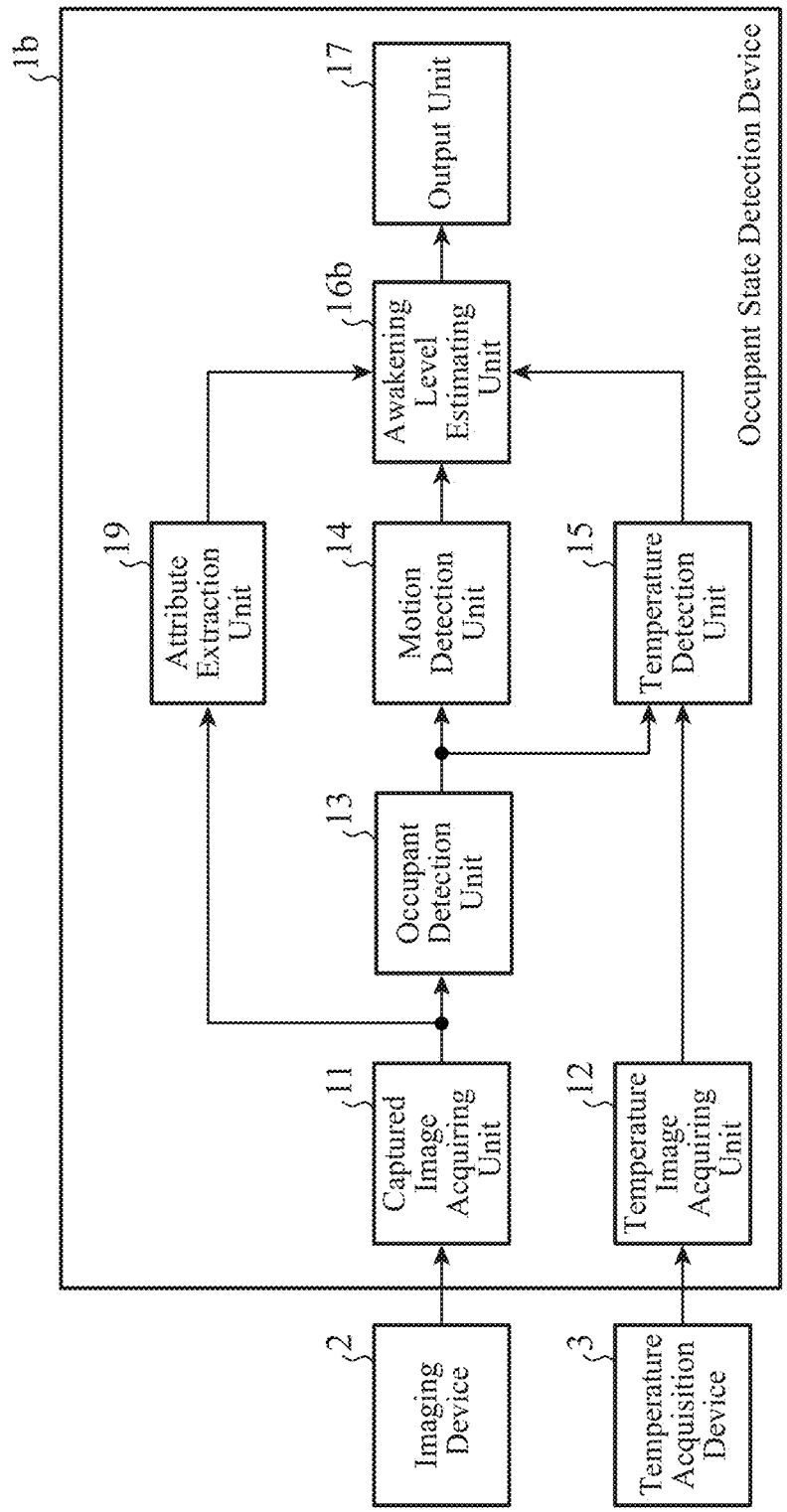
FIG. 6 is a diagram illustrating a configuration example of the occupant state detection device in a case where an awakening level of an occupant is estimated in consideration of an attribute of the occupant in the first embodiment.

FIG. 6 is a diagram illustrating a configuration example of an occupant state detection device 1b in a case where the awakening level of the occupant is estimated in consideration of the attribute of the occupant in the first embodiment.

In the occupant state detection device 1b illustrated in FIG. 6, the same components as those of the occupant state detection device 1 described with reference to FIG. 1 are denoted by the same reference numerals, and redundant description is omitted.

The occupant state detection device 1b is different from the occupant state detection device 1 described with reference to FIG. 1 in that the occupant state detection device 1b includes an attribute extraction unit 19.

In addition, in the occupant state detection device 1b, a specific operation of the awakening level estimating unit 16b is different from a specific operation of the awakening level estimating unit 16 in the occupant state detection device 1.

The attribute extraction unit 19 extracts the attribute of the occupant on the basis of the captured image acquired by the captured image acquiring unit 11. In the first embodiment, the attribute of the occupant is, for example, the age of the occupant, the gender of the occupant, or the physique of the occupant. Note that in the occupant state detection device 1b, the captured image acquiring unit 11 outputs the acquired captured image to the occupant detection unit 13 and the attribute extraction unit 19.

The attribute extraction unit 19 is only required to extract the attribute of the occupant from the captured image using a known image recognition processing technology.

The attribute extraction unit 19 outputs information (hereinafter, referred to as "occupant attribute information") regarding the extracted attribute of the occupant to the awakening level estimating unit 16b.

The awakening level estimating unit 16b estimates the awakening level of the occupant on the basis of the motion of the occupant detected by the motion detection unit 14, the temperature of the hand and the temperature of the face of the occupant detected by the temperature detection unit 15, and the attribute of the occupant extracted by the attribute extraction unit 19.

When the motion detection unit 14 detects the motion of the hand of the occupant, the awakening level estimating unit 16b estimates the awakening level of the occupant on the basis of the motion of the hand of the occupant. Specifically, the awakening level estimating unit 16b estimates that the occupant is in the awakening state because there is the motion of the hand of the occupant, and sets the awakening level of the occupant to "level 5". Note that the presence of the motion of the hand of the occupant means that the occupant is highly likely to be awakening.

On the other hand, when the motion detection unit 14 has not detected the motion of the hand of the occupant, the awakening level estimating unit 16b estimates the awakening level of the occupant on the basis of the motion of the occupant detected by the motion detection unit 14 and the temperature of the hand and the temperature of the face of the occupant detected by the temperature detection unit 15. Specifically, the awakening level estimating unit 16b estimates the awakening level of the occupant in accordance with the awakening level estimating rule constructed on the basis of the determination condition. At this time, the awakening level estimating unit 16b corrects the determination condition on the basis of the attribute of the occupant extracted by the attribute extraction unit 19. Then, the awakening level estimating unit 16b applies the corrected determination condition to the awakening level estimating rule to estimate the awakening level of the occupant.

The correction of the determination condition by the awakening level estimating unit 16b will be described with a specific example. In the following specific example, it is assumed that the determination conditions are (A) to (E) described above.

For example, the awakening level estimating unit 16b corrects the determination condition depending on the gender of the occupant. Specifically, for example, in a case where the occupant is a woman, the awakening level estimating unit 16b corrects the determination condition (E) to "the temperature of the hand is within –3° C. with respect to the temperature of the face". Generally, it is assumed that the body temperature of a woman is higher than that of a man. Therefore, in a case where the occupant is a woman, the awakening level estimating unit 16b corrects the determination condition (E) so as to narrow the width of the difference between the temperature of the hand and the temperature of the face, in which the degree indicating the awakening level is determined to be high.

Furthermore, for example, the awakening level estimating unit 16b corrects the determination condition depending on the age of the occupant. Specifically, for example, in a case where the occupant is elderly, the awakening level estimating unit 16b corrects the determination conditions (A) to (D) so that the condition in which the degree indicating the awakening level is determined to be high becomes severe, such that, the determination condition (A) is corrected to "the number of times the occupant blinks in the past 10 seconds is equal to or more than four", the determination condition (B) is corrected to "the time during which "the occupant closes his/her eyes" in the past 10 seconds is equal to or more than four seconds", the determination condition (C) is corrected to "the number of times "the occupant yawns" in the past three minutes is one or more", and the determination condition (D) is corrected to "the number of times "the head of the occupant wobbles" at an angle equal to or more than 20 degrees in the past five minutes is one or more".

Furthermore, for example, the awakening level estimating unit 16b corrects the determination condition depending on the physique of the occupant. Specifically, for example, in a case where the occupant is overweight, the awakening level estimating unit 16b corrects the determination condition (E) to "the temperature of the hand is within –3° C. with respect to the temperature of the face". Generally, it is assumed that an overweight person has a higher body temperature than an underweight person. Therefore, in a case where the occupant is overweight, the awakening level estimating unit 16b corrects the determination condition (E) so as to narrow the width of the difference between the temperature of the hand and the temperature of the face, in which the degree indicating the awakening level is determined to be high.

When estimating the awakening level of the occupant in accordance with the awakening level estimating rule to which the corrected determination condition is applied, the awakening level estimating unit 16b outputs the awakening level information to the output unit 17.

The operation of the occupant state detection device 1b configured as illustrated in FIG. 6 will be described.

The operation of the occupant state detection device 1b configured as illustrated in FIG. 6 is different from the operation of the occupant state detection device 1 described with reference to the flowchart of FIG. 4 in the specific operation in step ST408. Other specific operations (specific operations in steps ST401 to ST407 and step ST409) have already been described, and thus duplicate description will be omitted. Note that, in the occupant state detection device 1b, the specific operation in step ST407 is an operation in which the operation of the awakening level estimating unit 16, which has been already described, is replaced with the operation of the awakening level estimating unit 16b.

Furthermore, in the occupant state detection device 1b, before the operation in step ST408 is performed, the attribute extraction unit 19 extracts the attribute of the occupant on the basis of the captured image acquired by the captured image acquiring unit 11, and outputs the occupant attribute information to the awakening level estimating unit 16b.

In the occupant state detection device 1b, when the motion detection unit 14 has not detected the motion of the hand of the occupant ("NO" in step ST406), the awakening level estimating unit 16b estimates the awakening level of the occupant on the basis of the motion of the occupant detected by the motion detection unit 14 in step ST404, the temperature of the hand and the temperature of the face of the occupant detected by the temperature detection unit 15 in step ST405, and the attribute of the occupant extracted by the attribute extraction unit 19 (step ST408). Specifically, the awakening level estimating unit 16b estimates the awakening level of the occupant in accordance with the awakening level estimating rule constructed on the basis of the determination condition. At this time, the awakening level estimating unit 16b corrects the determination condition on the basis of the attribute of the occupant extracted by the attribute extraction unit 19. Then, the awakening level estimating unit 16b applies the corrected determination condition to the awakening level estimating rule to estimate the awakening level of the occupant.

The awakening level estimating unit 16b outputs the awakening level information to the output unit 17. Then, the operation of the occupant state detection device 1 proceeds to step ST409.

As described above, the occupant state detection device 1b acquires the captured image obtained by imaging the occupant and the temperature image indicating the temperature of the surface of the body of the occupant measured in a non-contact manner, and estimates the awakening level of the occupant on the basis of the motion of the occupant detected on the basis of the captured image, the temperature of the hand and the temperature of the face of the occupant detected on the basis of the temperature image, and the attribute of the occupant extracted on the basis of the captured image.

As a result, the occupant state detection device 1b can estimate the awakening level of the occupant on the basis of the temperature of the hand and the temperature of the face of the occupant regardless of the position where the occupant holds the steering wheel, and can estimate the awakening level in consideration of the attribute of the occupant.

In addition, the occupant state detection device 1b first determines whether or not the motion of the hand of the occupant has been detected when estimating the awakening level of the occupant, estimates the awakening level of the occupant on the basis of the motion of the hand of the occupant when the motion of the hand of the occupant has been detected, and estimates the awakening level of the occupant on the basis of the motion of the occupant, the temperature of the hand of the occupant, the temperature of the face of the occupant, and the attribute of the occupant when the motion of the hand of the occupant has not been detected.

As a result, the occupant state detection device 1b can reasonably estimate the awakening level of the occupant using the temperatures of the hand and the face of the occupant detected on the basis of the temperature image.

Note that, also in the occupant state detection device 1b, the awakening level estimating unit 16b does not need to use the temperature of the face of the occupant when estimating the awakening level of the occupant. That is, in a case where the motion of the hand has not been detected, the awakening level estimating unit 16b may estimate the awakening level of the occupant on the basis of the motion of the occupant detected by the motion detection unit 14, the temperature of the hand of the occupant detected by the temperature detection unit 15, and the attribute of the occupant extracted by the attribute extraction unit 19. As described above, the temperature of the occupant used when the awakening level estimating unit 16b estimates the awakening level of the occupant is only required to be at least the temperature of the hand of the occupant. Note that, in this case, the temperature detection unit 15 only needs to detect the temperature of the hand of the occupant as the temperature of the occupant.

In addition, the configuration of the occupant state detection device 1b as described above may be applied to the occupant state detection device 1a described with reference to FIG. 5. That is, the occupant state detection device 1a illustrated in FIG. 5 may include the attribute extraction unit 19.

In this case, the machine learning model 18 is a machine learning model that uses information regarding the motion of the occupant, information regarding the temperature of the hand and the temperature of the face of the occupant, and the attribute of the occupant as inputs, and outputs information indicating the degree of awakening of the occupant.

The awakening level estimating unit 16a estimates the awakening level of the occupant on the basis of the motion of the occupant detected by the motion detection unit 14, the temperature of the hand and the temperature of the face of the occupant detected by the temperature detection unit 15, the attribute of the occupant extracted by the attribute extraction unit 19, and the machine learning model 18.

When the motion detection unit 14 has detected the motion of the hand of the occupant, the awakening level estimating unit 16a estimates the awakening level of the occupant on the basis of the motion of the hand of the occupant.

On the other hand, when the motion detection unit 14 has not detected the motion of the hand of the occupant, the awakening level estimating unit 16a estimates the awakening level of the occupant on the basis of the motion of the occupant detected by the motion detection unit 14, the temperature of the hand and the temperature of the face of the occupant detected by the temperature detection unit 15, the attribute of the occupant extracted by the attribute extraction unit 19, and the machine learning model 18.

In addition, in the first embodiment described above, the temperature detection unit 15 may detect the temperature of the hand and the temperature of the face of the occupant from the temperature image acquired by the temperature image acquiring unit 12 without using the captured image after position assignment output from the occupant detection unit 13.

Figure 7:
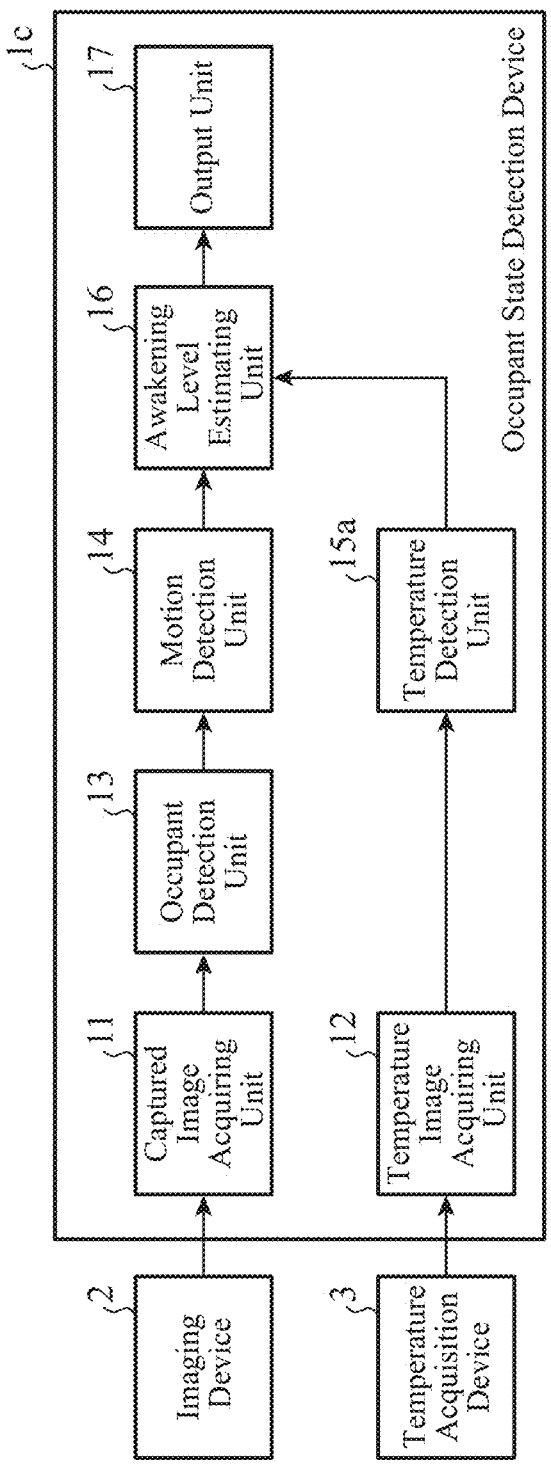
FIG. 7 is a diagram illustrating a configuration example of the occupant state detection device in a case where a temperature detection unit detects a temperature of an occupant without using a captured image after position assignment in the first embodiment.

FIG. 7 is a diagram illustrating a configuration example of an occupant state detection device 1c in a case where the temperature detection unit 15 detects the temperature of the occupant without using the captured image after position assignment in the first embodiment.

The configuration example of the occupant state detection device 1c illustrated in FIG. 7 is different from the configuration example of the occupant state detection device 1 illustrated in FIG. 1 in that there is no arrow indicating a flow of information from the occupant detection unit 13 to the temperature detection unit 15.

Furthermore, in the occupant state detection device 1c, the specific operation of a temperature detection unit 15a is different from the specific operation of the temperature detection unit in the occupant state detection device 1.

The temperature detection unit 15a detects the temperature of the hand and the temperature of the face of the occupant from the temperature distribution in the temperature image on the basis of the temperature image acquired by the temperature image acquiring unit 12.

As described above, in a case where the temperature detection unit 15a detects the temperature of the hand and the temperature of the face of the occupant without using the captured image after position assignment, it is not possible to perform alignment with respect to the position of the hand of the occupant and the position of the face of the occupant, so that the temperature detection accuracy by the temperature detection unit 15a decreases. However, the temperature detection unit 15a can omit the processing of aligning the captured image after position assignment and the temperature image.

Note that, in the occupant state detection device 1a described with reference to FIG. 5, the temperature detection unit 15 may detect the temperature of the hand and the temperature of the face of the occupant from the temperature image acquired by the temperature image acquiring unit 12 without using the captured image after position assignment output from the occupant detection unit 13.

In addition, in the above-described first embodiment, in a case where the temperature acquisition device 3 outputs a relatively high-resolution temperature image, the temperature detection unit 15, 15a may detect a temperature of a more detailed face part with respect to the temperature of the face of the occupant on the basis of the temperature image. Specifically, the temperature detection unit 15, 15a may detect the forehead temperature or the cheek temperature as the face temperature of the occupant, for example.

In general, it is assumed that the forehead temperature or the cheek temperature is close to the deep body temperature of a person. On the other hand, since the nose is the peripheral portion, similarly to the hand, the blood flow rate at the nose increases and the temperature at the nose increases when the person feels drowsy.

The temperature detection unit 15, 15a subdivides the temperature of the face based on the parts, and detects the forehead temperature or the cheek temperature, which is assumed to be close to the deep body temperature of the person, as the temperature of the face of the occupant except for the nose and the like, which are the peripheral portions, so that the accuracy of the degree of awakening of the occupant estimated by using the temperature of the face by the awakening level estimating unit 16, 16a, 16b can be improved.

In addition, in the first embodiment, the occupant detection unit 13 outputs information indicating the detected position of the eye of the occupant, position of the mouth of the occupant, position of the body of the occupant, position of the hand of the occupant, or position of the face of the occupant to the motion detection unit 14 and the temperature detection units 15, 15a. However, this is merely an example.

The occupant detection unit 13 may narrow the information to necessary information among the information indicating the position of the eye of the occupant, the position of the mouth of the occupant, the position of the body of the occupant, the position of the hand of the occupant, or the position of the face of the occupant, in the motion detection unit 14 or the temperature detection unit 15, and then output the narrowed information to the motion detection unit 14 or the temperature detection unit 15, 15a.

Specifically, the occupant detection unit 13 may output information (hereinafter, referred to as "eye-mouth-face-body position information") regarding the position of the eye of the occupant, the position of the mouth of the occupant, the position of the face of the occupant, and the position of the body of the occupant to the motion detection unit 14, and output information (hereinafter, referred to as "face-hand position information") regarding the position of the face of the occupant and the position of the hand of the occupant to the temperature detection unit 15, 15a.

In this case, the motion detection unit 14 detects the motion of the eye of the occupant, the motion of the mouth of the occupant, the motion of the face of the occupant, or the motion of the body of the occupant on the basis of the eye-mouth-face-body position information output from the occupant detection unit 13. In addition, the temperature detection unit 15, 15a detects the temperature of the hand and the temperature of the face of the occupant on the basis of the face-hand position information output from the occupant detection unit 13.

In addition, in the first embodiment described above, the motion detection unit 14 may have the function of the occupant detection unit 13. That is, the motion detection unit 14 may have a function of detecting occupant information. Note that, in this case, the motion detection unit 14 outputs the captured image after position assignment to the temperature detection unit 15. In this case, the occupant state detection device 1, 1a, 1b, 1c can be configured not to include the occupant detection unit 13. Furthermore, in this case, regarding the operation of the occupant state detection device 1, 1a, 1b, 1c described with reference to the flowchart of FIG. 4, the operation in step ST403 is performed by the motion detection unit 14.

In the first embodiment described above, the occupant is the driver of the vehicle, but this is merely an example. The occupant is an occupant of the vehicle other than the driver, and the occupant state detection device 1, 1a, 1b can also estimate the awakening level of the occupant other than the driver.

In the first embodiment described above, the occupant state detection device 1, 1a, 1b is mounted on the vehicle and estimates the awakening level of the occupant of the vehicle, but this is merely an example. The occupant state detection device 1, 1a, 1b can also estimate the awakening level of the occupant of a mobile object in various mobile objects.

Figure 8A:
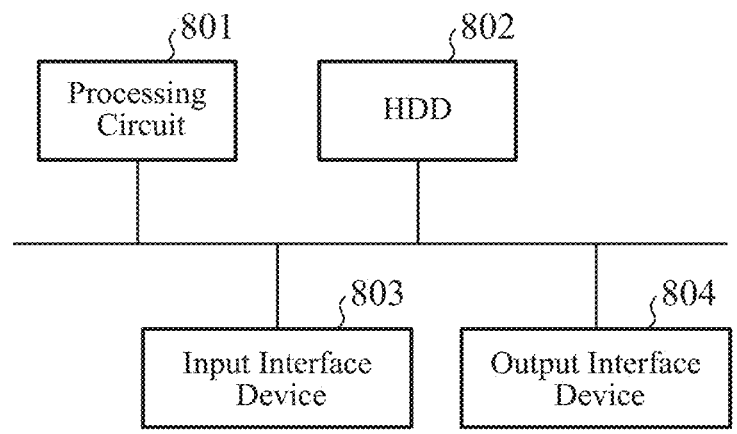
FIGS. 8A and 8B are diagrams illustrating an example of a hardware configuration of the occupant state detection device according to the first embodiment.
Figure 8B:
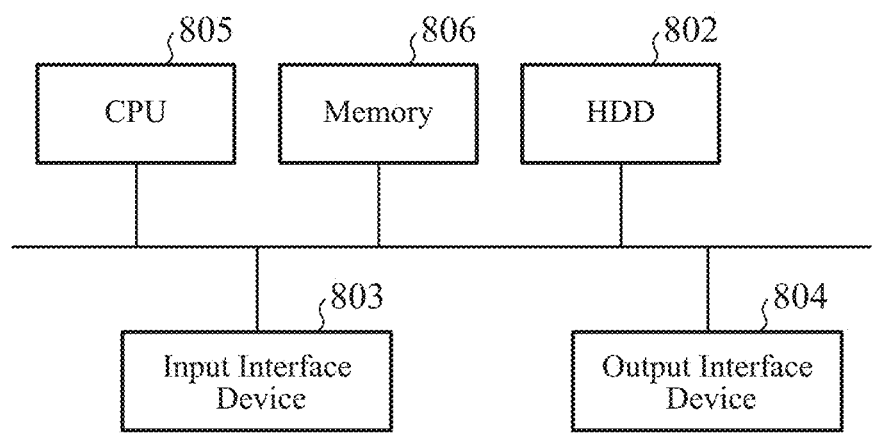

FIGS. 8A and 8B are diagrams illustrating an example of a hardware configuration of the occupant state detection device 1, 1a, 1b, 1c according to the first embodiment. Each of the occupant state detection devices 1, 1a, 1b, and 1c has a hardware configuration as illustrated in FIGS. 8A and 8B.

In the first embodiment, the functions of the captured image acquiring unit 11, the temperature image acquiring unit 12, the occupant detection unit 13, the motion detection unit 14, the temperature detection unit 15, 15a, the awakening level estimating unit 16, 16a, 16b, the output unit 17, and the attribute extraction unit 19 are implemented by a processing circuit 801. That is, the occupant state detection device 1, 1a, 1b, 1c includes the processing circuit 801 for performing control to estimate the degree of awakening of the occupant of the mobile object.

The processing circuit 801 may be dedicated hardware as illustrated in FIG. 8A, or may be a central processing unit (CPU) 805 that executes a program stored in a memory 806 as illustrated in FIG. 8B.

In a case where the processing circuit 801 is dedicated hardware, the processing circuit 801 corresponds to, for example, a single circuit, a composite circuit, a programmed processor, a parallel programmed processor, a system-on-a-chip (SoC), an application specific integrated circuit (ASIC), a field-programmable gate array (FPGA), or a combination thereof.

In a case where the processing circuit 801 is the CPU 805, the functions of the captured image acquiring unit 11, the temperature image acquiring unit 12, the occupant detection unit 13, the motion detection unit 14, the temperature detection unit 15, 15a, the awakening level estimating unit 16, 16a, 16b, the output unit 17, and the attribute extraction unit 19 are implemented by software, firmware, or a combination of software and firmware. That is, the captured image acquiring unit 11, the temperature image acquiring unit 12, the occupant detection unit 13, the motion detection unit 14, the temperature detection unit 15, 15a, the awakening level estimating unit 16, 16a, 16b, the output unit 17, and the attribute extraction unit 19 are implemented by the CPU 805 that executes a program stored in a hard disk drive (HDD) 802, the memory 806, or the like, or the processing circuit 801 such as a system large-scale integration (LSI). In addition, it can also be said that the program stored in the HDD 802, the memory 806, or the like causes a computer to execute a procedure or a method performed by the captured image acquiring unit 11, the temperature image acquiring unit 12, the occupant detection unit 13, the motion detection unit 14, the temperature detection unit 15, 15a, the awakening level estimating unit 16, 16a, 16b, the output unit 17, and the attribute extraction unit 19. Here, the memory 806 corresponds to, for example, a nonvolatile or volatile semiconductor memory such as a RAM, a read only memory (ROM), a flash memory, an erasable programmable read only memory (EPROM), or an electrically erasable programmable read-only memory (EEPROM), a magnetic disk, a flexible disk, an optical disk, a compact disk, a mini disk, a digital versatile disc (DVD), or the like.

Note that the functions of the captured image acquiring unit 11, the temperature image acquiring unit 12, the occupant detection unit 13, the motion detection unit 14, the temperature detection unit 15, 15a, the awakening level estimating unit 16, 16a, 16b, the output unit 17, and the attribute extraction unit 19 may be partially implemented by dedicated hardware and partially implemented by software or firmware. For example, the functions of the captured image acquiring unit 11, the temperature image acquiring unit 12, and the output unit 17 can be implemented by the processing circuit 801 as dedicated hardware, and the functions of the occupant detection unit 13, the motion detection unit 14, the temperature detection unit 15, 15a, the awakening level estimating unit 16, 16a, 16b, and the attribute extraction unit 19 can be implemented by the processing circuit 801 reading and executing programs stored in the memory 806.

The storage unit (not illustrated) uses the memory 806. Note that this is an example, and the storage unit (not illustrated) may be configured by the HDD 802, a solid state drive (SSD), a DVD, or the like.

In addition, the occupant state detection device 1, 1a, 1b, 1c includes an input interface device 803 and an output interface device 804 that perform wired communication or wireless communication with a device such as the imaging device 2 or the temperature acquisition device 3.

As described above, according to the first embodiment, the occupant state detection device 1, 1b, 1c is configured to include the captured image acquiring unit 11 that acquires the captured image obtained by imaging the occupant, the temperature image acquiring unit 12 that acquires the temperature image indicating the temperature of the surface of the body of the occupant measured in a non-contact manner, the motion detection unit 14 that detects the motion of the occupant on the basis of the captured image acquired by the captured image acquiring unit 11, the temperature detection unit 15, 15a that detects the temperature of the hand of the occupant on the basis of the temperature image acquired by the temperature image acquiring unit 12, and the awakening level estimating unit 16, 16b that estimates the awakening level of the occupant on the basis of the motion of the occupant detected by the motion detection unit 14 and the temperature of the hand of the occupant detected by the temperature detection unit 15, 15a.

Therefore, the occupant state detection device 1, 1b, 1c can estimate the awakening level of a person on the basis of the temperature of the hand of the person regardless of the position where the person (occupant) holds the steering wheel.

Furthermore, according to the first embodiment, in the occupant state detection device 1, 1b, 1c, the motion of the occupant detected by the motion detection unit 14 includes the motion of the hand of the occupant, and the awakening level estimating unit 16, 16b is configured to estimate the awakening level of the occupant on the basis of the motion of the hand of the occupant when the motion detection unit 14 has detected the motion of the hand of the occupant, and estimate the awakening level of the occupant on the basis of the motion of the occupant detected by the motion detection unit 14 and the temperature of the hand of the occupant detected by the temperature detection units 15, 15a when the motion detection unit 14 has not detected the motion of the hand of the occupant.

Therefore, the occupant state detection device 1, 1b, 1c can reasonably estimate the awakening level of the occupant using the temperatures of the hand and the face of the occupant detected on the basis of the temperature image.

Furthermore, according to the first embodiment, the occupant state detection device 1a includes the captured image acquiring unit 11 that acquires the captured image obtained by imaging the occupant, the temperature image acquiring unit 12 that acquires the temperature image indicating the temperature of the surface of the body of the occupant measured in a non-contact manner, the motion detection unit 14 that detects the motion of the occupant on the basis of the captured image acquired by the captured image acquiring unit 11, the temperature detection unit 15 that detects the temperature of the hand of the occupant on the basis of the temperature image acquired by the temperature image acquiring unit 12, and the awakening level estimating unit 16a that estimates the awakening level of the occupant on the basis of the information regarding the motion of the occupant detected by the motion detection unit 14, the information regarding the temperature of the hand of the occupant detected by the temperature detection unit 15, and the machine learning model 18.

Therefore, the occupant state detection device 1a can estimate the awakening level of a person on the basis of the temperature of the hand of the person regardless of the position where the person (occupant) holds the steering wheel.

Furthermore, according to the first embodiment, in the occupant state detection device 1a, the motion of the occupant detected by the motion detection unit 14 includes the motion of the hand of the occupant, and the awakening level estimating unit 16a is configured to estimate the awakening level of the occupant on the basis of the motion of the hand of the occupant when the motion detection unit 14 has detected the motion of the hand of the occupant, and to estimate the awakening level of the occupant on the basis of the machine learning model 18 when the motion detection unit 14 has not detected the motion of the hand of the occupant.

Therefore, the occupant state detection device 1a can reasonably estimate the awakening level of the occupant using the temperatures of the hand and the face of the occupant detected on the basis of the temperature image.

Note that, in the first embodiment described above, the occupant state detection device 1, 1a, 1b, 1c is an in-vehicle device mounted on the vehicle, and the captured image acquiring unit 11, the temperature image acquiring unit 12, the occupant detection unit 13, the motion detection unit 14, the temperature detection unit 15, 15a, the awakening level estimating unit 16, 16a, 16b, the output unit 17, and the attribute extraction unit 19 are included in the occupant state detection device 1, 1a, 1b, 1c.

It is not limited thereto, and the occupant state detection system may be configured by the in-vehicle device and the server, assuming that some of the captured image acquiring unit 11, the temperature image acquiring unit 12, the occupant detection unit 13, the motion detection unit 14, the temperature detection unit 15, 15a, the awakening level estimating unit 16, 16a, 16b, the output unit 17, and the attribute extraction unit 19 are mounted in the in-vehicle device of the vehicle, and the others are provided in the server connected to the in-vehicle device via the network.

Furthermore, in the present disclosure, any component of the embodiment can be modified, or any component of the embodiment can be omitted.

INDUSTRIAL APPLICABILITY

Since the occupant state detection device according to the present disclosure is configured to be able to estimate the awakening level of a person on the basis of the temperature of the hand of the person regardless of the position where the person holds the steering wheel, the occupant state detection device can be applied to the occupant state estimation device that estimates the awakening level of the occupant in the mobile object.

REFERENCE SIGNS LIST 1, 1a, 1b, 1c: occupant state detection device, 2: imaging device, 3: temperature acquisition device, 11: captured image acquiring unit, 12: temperature image acquiring unit, 13: occupant detection unit, 14: motion detection unit, 15, 15a: temperature detection unit, 16, 16a, 16b: awakening level estimating unit, 17: output unit, 18: machine learning model, 19: attribute extraction unit, 801: processing circuit, 802: HDD, 803: input interface device, 804: output interface device, 805: CPU, 806: memory

The invention claimed is:

1. An occupant state detection device comprising:
processing circuitry configured to
acquire a captured image obtained by imaging an occupant;
acquire a temperature image indicating a temperature of a surface of a body of the occupant measured in a non-contact manner;
detect a motion of the occupant on a basis of the acquired captured image;
detect a temperature of a hand of the occupant on a basis of the acquired temperature image
estimate an awakening level of the occupant on a basis of the detected motion of the occupant and the detected temperature of the hand of the occupant;
estimate the awakening level of the occupant on a basis of the motion of the hand of the occupant in response to the motion of the occupant including a motion of the hand of the occupant such that a motion of the hand of the occupant has been detected; and
estimate the awakening level of the occupant on a basis of the detected motion of the occupant and the detected temperature of the hand of the occupant in response to the motion of the occupant not including a motion of the hand of the occupant such that a motion of the hand of the occupant has not been detected; and
control a vehicle system in response to the estimated awakening level of the occupant.

2. The occupant state detection device according to claim 1,
wherein the processing circuitry detects, as the motion of the occupant, a motion of an eye of the occupant, a motion of a mouth of the occupant, a motion of a body of the occupant, a motion of the hand of the occupant, or a motion of a face of the occupant.

3. The occupant state detection device according to claim 1,
wherein the processing circuitry detects a temperature of the hand of the occupant and a temperature of a face of the occupant, and
the processing circuitry estimates an awakening level of the occupant on a basis of the detected motion of the occupant and the temperature of the hand and the detected temperature of the face of the occupant.

4. An occupant state detection device comprising:
processing circuitry configured to
acquire a captured image obtained by imaging an occupant;
acquire a temperature image indicating a temperature of a surface of a body of the occupant measured in a non-contact manner;
detect a motion of the occupant on a basis of the acquired captured image;
detect a temperature of a hand of the occupant on a basis of the acquired temperature image;
estimate an awakening level of the occupant on a basis of information regarding the detected motion of the occupant, information regarding the detected temperature of the hand of the occupant, and a machine learning model;
estimate the awakening level of the occupant on a basis of the motion of the hand of the occupant in response to the motion occupant including a motion of the hand of the occupant such that a motion of the of the hand of the occupant has been detected; and
estimate the awakening level of the occupant on a basis of the machine learning model in response to the motion of the occupant not including a motion of the hand of the occupant such that a motion of the hand of the occupant has not been detected; and
control a vehicle system in response to the estimated awakening level of the occupant.

5. An occupant state detection method comprising:
acquiring a captured image obtained by imaging an occupant;
acquiring a temperature image indicating a temperature of a surface of a body of the occupant measured in a non-contact manner;
detecting a motion of the occupant on a basis of the captured image having been acquired;
detecting a temperature of a hand of the occupant on a basis of the acquired temperature image;
estimating an awakening level of the occupant on a basis of information regarding the detected motion of the occupant, information regarding the detected temperature of the hand of the occupant, and a machine learning model;
estimating the awakening level of the occupant on a basis of the motion of the hand of the occupant in response to the motion occupant including a motion of the hand of the occupant such that a motion of the of the hand of the occupant has been detected; and
estimating the awakening level of the occupant on a basis of the machine learning model in response to the motion of the occupant not including a motion of the hand of the occupant such that a motion of the hand of the occupant has not been detected; and
controlling a vehicle system in response to the estimated awakening level of the occupant.

* * * * *